(12) United States Patent
Leroux et al.

(10) Patent No.: US 6,800,403 B2
(45) Date of Patent: Oct. 5, 2004

(54) TECHNIQUES TO CHARACTERIZE ISO-DENSE EFFECTS FOR MICRODEVICE MANUFACTURE

(75) Inventors: Pierre Leroux, San Antonio, TX (US); David Ziger, San Antonio, TX (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 198 days.

(21) Appl. No.: 10/175,367

(22) Filed: Jun. 18, 2002

(65) Prior Publication Data

US 2003/0232253 A1 Dec. 18, 2003

(51) Int. Cl.[7] ................................................. G03F 9/00
(52) U.S. Cl. ................................................ 430/5; 430/30
(58) Field of Search ........................................ 430/5, 30

(56) References Cited

U.S. PATENT DOCUMENTS

| | | |
|---|---|---|
| 5,214,492 A | 5/1993 | LoBianco et al. |
| 5,280,437 A | 1/1994 | Corliss |
| 5,392,113 A | 2/1995 | Sayka et al. |
| 5,407,785 A | 4/1995 | Leroux |
| 5,438,413 A | 8/1995 | Mazor et al. |
| 5,545,593 A | 8/1996 | Watkins et al. |
| 5,617,340 A | 4/1997 | Cresswell et al. |
| 5,629,772 A | 5/1997 | Ausschnitt |
| 5,655,110 A | 8/1997 | Krivokapic et al. |
| 5,699,282 A | 12/1997 | Allen et al. |
| 5,776,645 A | 7/1998 | Barr et al. |
| 5,780,208 A | 7/1998 | Ziger et al. |
| 5,790,254 A | 8/1998 | Ausschnitt |
| 5,830,610 A | 11/1998 | Leroux et al. |
| 5,835,227 A | 11/1998 | Grodnensky et al. |
| 5,856,052 A | 1/1999 | Leroux |
| 5,876,883 A | 3/1999 | Leroux |
| 5,902,703 A | 5/1999 | Leroux et al. |
| 5,962,173 A | 10/1999 | Leroux et al. |
| 5,982,044 A | 11/1999 | Lin et al. |
| 6,077,756 A | 6/2000 | Lin et al. |
| 6,079,256 A | 6/2000 | Bareket |
| 6,127,071 A | 10/2000 | Lu |
| 6,127,075 A | 10/2000 | Hsu |
| 6,128,089 A | 10/2000 | Ausschnitt et al. |
| 6,130,750 A | 10/2000 | Ausschnitt et al. |
| 6,137,578 A | 10/2000 | Ausschnitt |
| 6,185,323 B1 | 2/2001 | Archie et al. |
| 6,218,200 B1 | 4/2001 | Chen et al. |
| 6,225,639 B1 | 5/2001 | Adams et al. |
| 6,280,887 B1 | 8/2001 | Lu |
| 6,301,008 B1 | 10/2001 | Ziger et al. |
| 6,303,253 B1 | 10/2001 | Lu |
| 6,350,548 B1 | 2/2002 | Leidy et al. |
| 6,596,444 B2 * | 7/2003 | Buck .............................. 430/5 |

OTHER PUBLICATIONS

"Minimising Optical Overlay Measurement Errors", Smith et al., *SPIE*, vol. 1926, pp. 450–462 (Dated 1993).

"Sub–0.35–micron critical dimension metrology using atomic force microscopy", Wilder et al., *SPIE*, vol. 2725, pp. 540–554 (Dated 1996).

"Combined level–to–level and within–level overlay control", Ausschnitt et al., *SPIE*, vol. 4689, pp. 1–13 (Dated 2002).

\* cited by examiner

*Primary Examiner*—Christopher G. Young
(74) *Attorney, Agent, or Firm*—Peter Zawilski

(57) ABSTRACT

A technique is provided to define a pattern (100) on a substrate (70) that includes a dense region with a number of features (101) and an isolated feature region comprised of at least a part of one of the features (101). The dense feature region has a greater feature density than the isolated feature region. A reference feature (103) is measured at a number of different points relative to the isolated feature region and the dense feature region with a measurement tool (75). An iso-dense effect is determined from these measurements.

12 Claims, 5 Drawing Sheets

TECHNIQUES TO CHARACTERIZE ISO-DENSE EFFECTS FOR MICRODEVICE MANUFACTURE

BACKGROUND OF THE INVENTION

The present invention relates to characterization of the iso-dense effect. More particularly, but not exclusively, the present invention relates to determining the iso-dense effect for microdevice manufacture.

To increase the speed of electronic devices, it is often desirable to decrease the critical dimension of various semiconductor components. Concomitantly, functionality of many integrated circuit devices may be increased by reducing the size of individual components so that the component density, and correspondingly the number and complexity of integrated circuits formed from the components may be increased. Unfortunately, as the critical dimension of semiconductor devices is deeply scaled down into the submicron range (<0.5 micron), various shortcomings of the processes used to make such devices can become of greater concern.

For lithographic processes aimed at forming devices with dimensions in the submicron range, the iso-dense effect can become more prominent. The iso-dense effect results in a difference in transfer dimension for dense features as compared to features that are more greatly spaced apart. This phenomenon is commonly encountered as a linewidth transfer difference between an isolated line of submicron width and a denser lines of comparable width with submicron spacing. Wilder and Singh et al., *Sub-0.35-Micron Critical Dimension Metrology Using Atomic Force Microscopy*, SPIE Proceedings, volume 2725, pages 540–554 (published 1996) provides information concerning existing techniques to evaluate the iso-dense effect and is incorporated by reference in its entirety herein.

Notably, characterizing the iso-dense effect can be complicated by the fact that measurement tools, such as a Scanning Electron Microscope (SEM), can be sensitive to the iso-dense condition. As a result, special tools are sometimes used, such as the Atomic Force Microscope (AFM), and/or electrical measurements are made; however, these approaches can be slow and expensive, and generally cannot be performed in real time with the desired manufacturing process. Other measurement schemes include application of a Transmission Electron Microscope (TEM); however, such schemes are typically destructive and require long sample preparation times. Consequently, further contributions are needed in this area of technology.

SUMMARY OF THE INVENTION

One embodiment of the present invention includes a unique technique to characterize the iso-dense effect. Other embodiments of the present invention include unique systems, methods, and apparatus to determine the iso-dense effect for microdevice manufacture.

A further embodiment of the present invention includes the definition of a pattern on a substrate for manufacture of a microdevice. This pattern includes a dense feature region and an isolated feature region. A portion of one or more features in the dense feature region are removed and one or more measurements are made corresponding to at least one of the remaining features after this removal. An iso-dense effect is determined from the measurements.

A further embodiment includes: defining a pattern on a substrate that includes a dense region of features and an isolated feature region comprised of at least a part of one of the features; measuring at least one of these features at a number of different points relative to the isolated and dense regions with a measurement tool; and determining an iso-dense effect for the measurement tool from these measurements.

Still another embodiment of the present invention includes a mask having a central portion to define a layer of one or more integrated circuits, a first end portion to define a first pattern including a dense region of features, and a second end portion opposite the first end portion to define a second pattern including one or more windows. During operation, the mask is arranged to overlap one or more of the features of the first pattern when making one field with one or more windows of the second pattern when making an adjacent field. From these overlapping patterns, a set of measurable marks are provided to determine an iso-dense effect.

Yet another embodiment includes a device having an iso-dense effect evaluation pattern comprised of a number of approximately parallel line segments, with at least one of the line segments being provided as a reference mark measurable at different points to determine one or more iso-dense effects. In one form, the reference mark extends from a dense region of the line segments to an isolated region to provide an isolated portion. This isolated portion is separated from the other line segments by a distance greater than the minimum spacing of the line segments in the dense region.

Accordingly, one object of the present invention is to provide a unique technique to characterize an iso-dense effect.

Another object of the present invention is to provide a unique method, system, or apparatus to determine an iso-dense effect for the manufacture of a microdevice.

Further objects, features, aspects, forms, embodiments, benefits, and advantages of the present invention shall become apparent from the description and figures contained herein.

DETAILED DESCRIPTION

Figure 1:
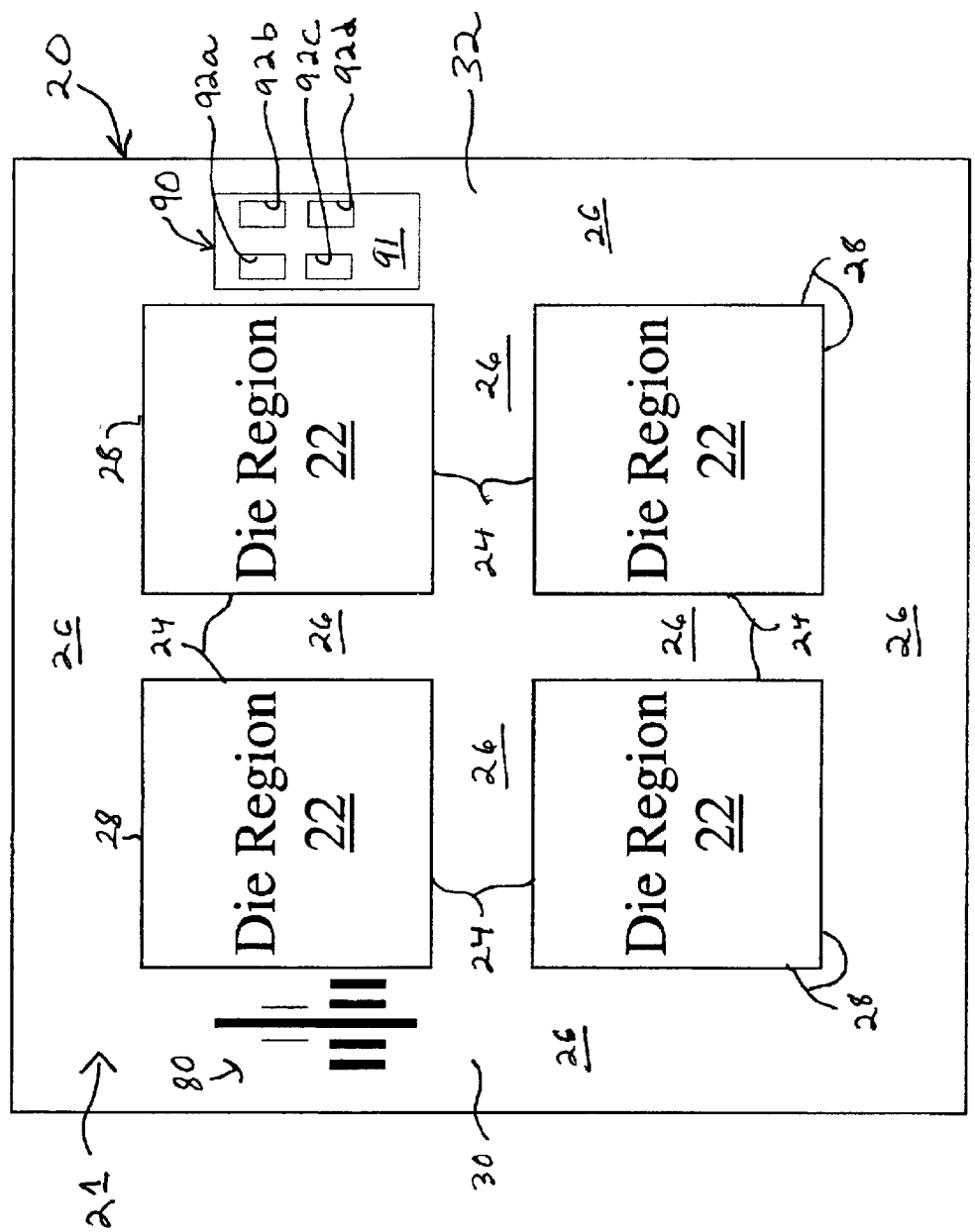
FIG. 1 is a diagrammatic view of a photolithographic mask for manufacturing integrated circuitry.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
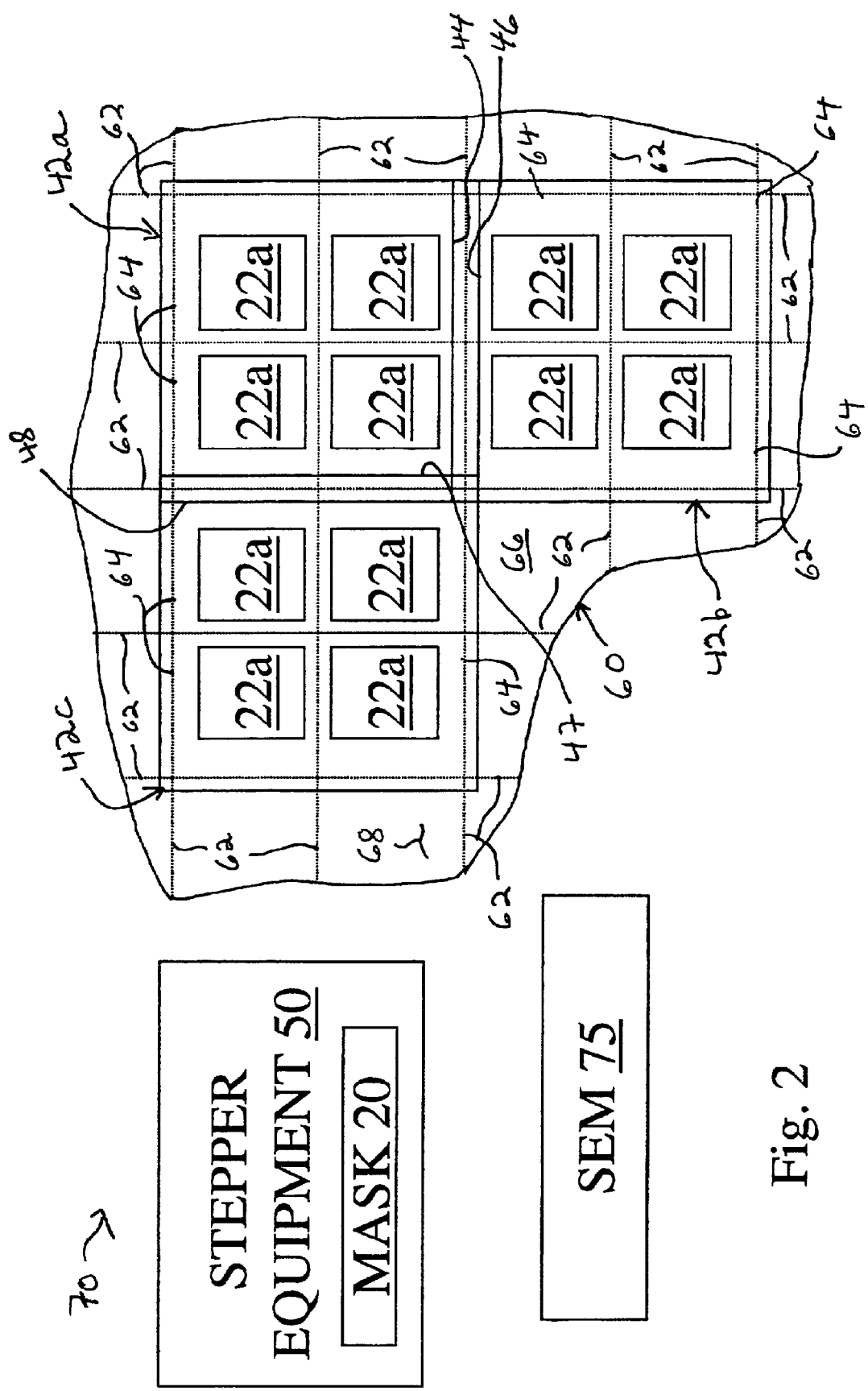
FIG. 2 is a diagrammatic view of a wafer processing system that operates with the mask of FIG. 1.

FIG. 1 depicts mask 20 of one embodiment of the present invention. Mask 20 includes a pattern 21 to photolithographically define features for the manufacture of integrated circuitry. Referring additionally to wafer processing system 70 of FIG. 2, mask 20 is utilized with stepper equipment 50 to repetitively define pattern 21 on semiconductor wafer 60. Wafer 60 is illustrated with kerfs (or scribe lines) 62 arranged in a grid. Kerfs 62 are schematically represented by lines of a square dot pattern, and only a cutaway portion of wafer 60 is schematically shown in FIG. 2 to enhance clarity. Typically, a complete wafer has a generally circular profile and may include a flat for orientation purposes. Nonetheless, in other embodiments wafer 60 may be shaped differently.

Each rectangular or square area defined by the grid of kerfs 62 is used to form an integrated circuit device 64 (only a few of which are designated by reference numerals to preserve clarity). Devices 64 can be separated from one another along kerfs 62 to form corresponding die at a later stage of manufacture (not shown). Wafer 60 is alternatively designated substrate 66, and may include one or more layers, and/or may be comprised of one or more different materials.

Mask 20 is arranged to provide a field shot with a central portion defining an integrated circuitry pattern corresponding to four central die pattern regions 22 at once. Central die pattern regions 22 are separated from one another at inner borders 24 by kerf or scribe line regions 26 positioned therebetween. Regions 26 also frame regions 22 at outer borders 28. Regions 26 of mask 20 include side end portion 30 opposite side end portion 32. End portion 30 includes mask pattern 80 and end portion 32 includes mask pattern 90.

In FIG. 2, three representative field shots 42a, 42b, and 42c are illustrated on substrate 66, which were shot with equipment 50 using mask 20. Each field shot 42a, 42b, and 42c formed with mask 20 is represented by a square formed of solid lines that encloses four central die regions 22a defined with central die pattern regions 22. It should be understood that additional field shots would typically be made along the useable area of wafer 60. This arrangement reveals an overlap in the field shots 42a, 42b, and 42c that has been exaggerated in FIG. 2 to enhance clarity. As depicted, upper end 44 of field shot 42b overlaps lower end 46 of field shot 42a and side 47 of field shot 42c overlaps side 48 of field shot 42a. This overlap corresponds to the overlay of end portion 32 on end portion 30, such that pattern 90 of one field shot overlays pattern 80 of a subsequent field shot to selectively double expose a portion of the features defined with pattern 80.

Figure 3:
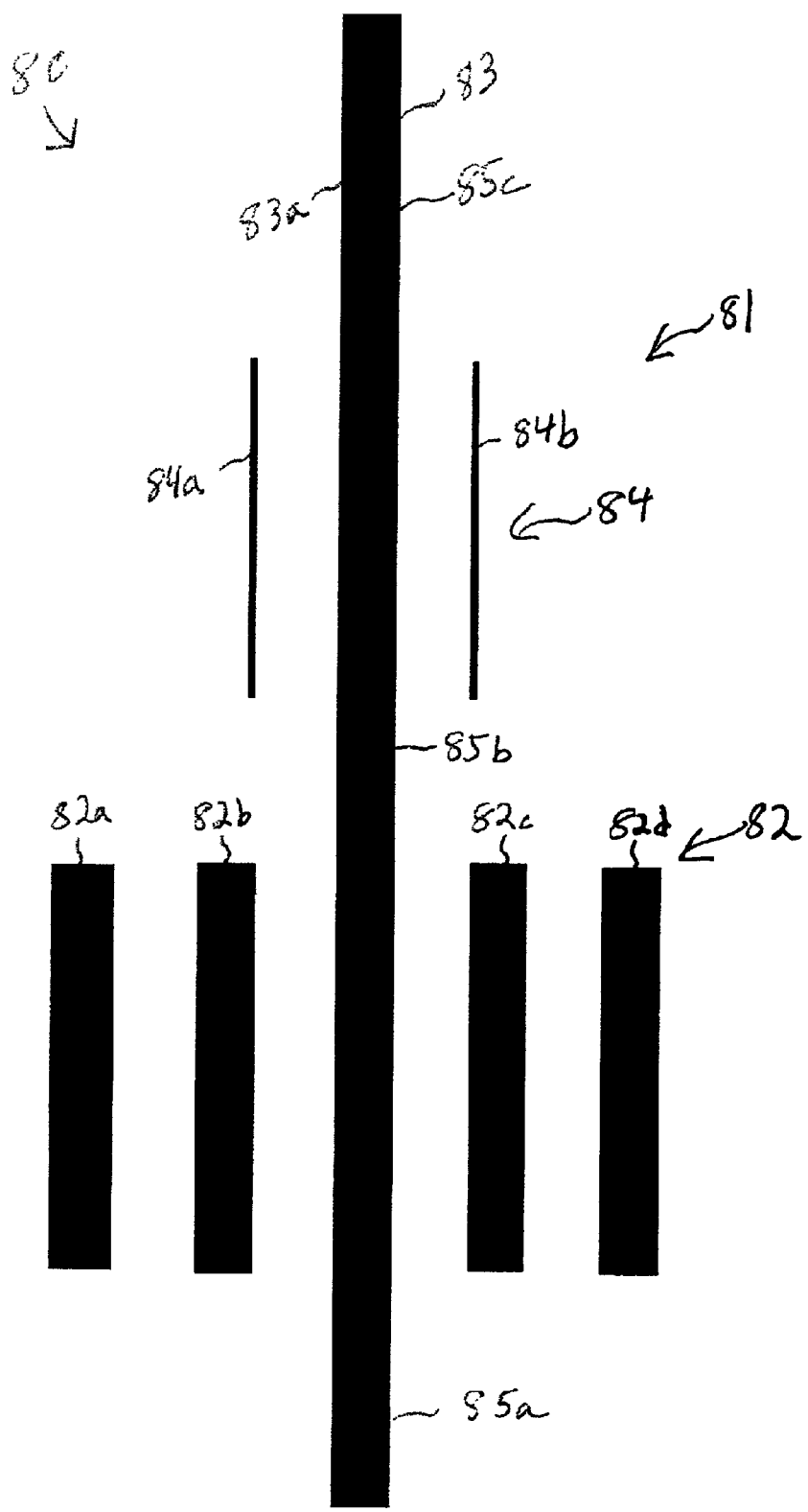
FIG. 3 is a partial, diagrammatic view of the mask shown in FIG. 1, illustrating a mask pattern in greater detail.

Turning to FIG. 3, mask pattern 80 is described in greater detail. Pattern 80 includes a number of features 81 in the form of approximately parallel line segments that are opaque to electromagnetic radiation used to perform lithographic processes with mask 20. Features 81 are arranged to provide dense feature region 82, in which features 81 are alternatively designated line segments 82a, 82b, 82c, and 82d; and reference feature 83, which is alternatively designated line segment 83a. Pattern 80 also includes assist feature region 84, including assist features 84a and 84b in the form of line segments. In other regions 85a, 85b, and 85c, feature 83 is spatially isolated relative to the remaining features. It should be understood that the number of features per unit area in dense feature region 82 is greater than features per unit area in regions 85a, 86, and 85c.

Referring back to FIG. 1, pattern 90 includes a blocking area 91 that is opaque to electromagnetic radiation used for lithographic processing with mask 20. Blocking area 91 defines windows 92a, 92b, 92c, and 92d therethrough for selectively exposing portions of a field to such radiation. Windows 92a–92d are arranged to remove certain parts of the features resulting on substrate 66 from exposure to pattern 80. The lithographic processing performed to provide an iso-dense effect evaluation pattern on substrate 66 is next described in greater detail.

Figure 5:
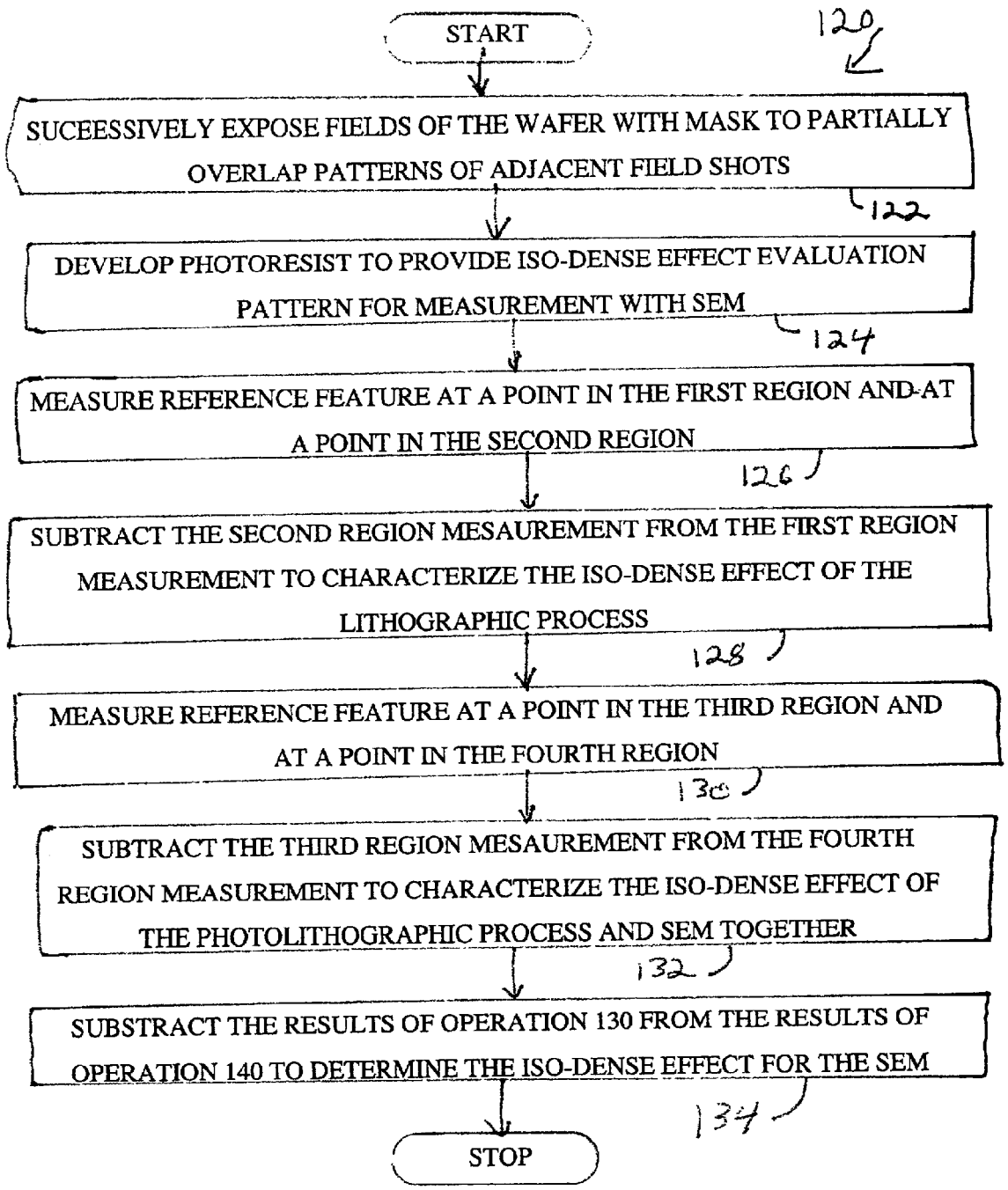
FIG. 5 is a flowchart of a process for characterizing iso-dense effects during the manufacture of integrated circuitry with the mask of FIG. 1.

FIG. 5 depicts a flowchart of iso-dense effect evaluation process 120. In operation 122 of process 120, mask 20, stepper equipment 50, and wafer 60 are arranged in a standard manner, with substrate 66 including a positive photoresist film 68 (see FIG. 2). The photoresist film 68 is selectively exposed to electromagnetic radiation of an appropriate type through portions of mask 20 transparent to such radiation, while being blocked by other portions such as features 81 of pattern 80 and area 91 of pattern 90. These exposures are performed for each successive field that is shot with mask 20, incrementing with stepper equipment 50 from one field to the next. As one field is shot, the side adjacent a previously shot field causes an overlap such that pattern 90 overlays features imparted to substrate 66 with pattern 80 for this previously shot field. In operation 124, the photoresist film 68 is developed to provide a metrology pattern of marks corresponding to these features.

Figure 4:
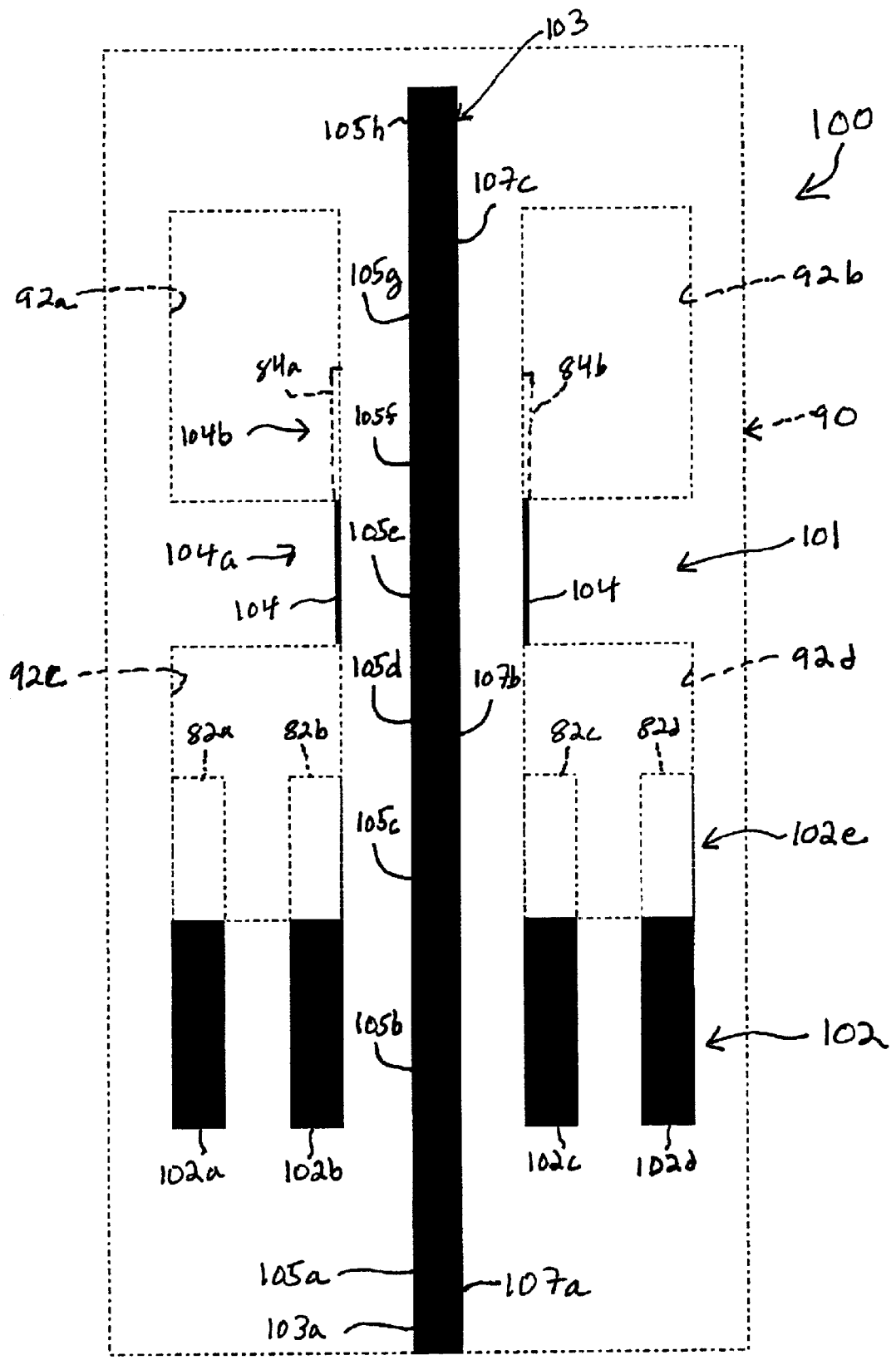
FIG. 4 is a partial, diagrammatic view of an iso-dense effect evaluation pattern provided with the system of FIG. 2 using the mask of FIG. 1.

As shown in FIG. 4, this resulting iso-dense effect evaluation pattern of developed photoresist features is designated by reference numeral 100. Pattern 100 includes features or marks 101 on wafer 60 which correspond generally to features 81, except that parts of line segments 82a, 82b, 82c, and 82d have been removed by double exposure through windows 92c and 92d of pattern 90; and parts of assist features 84a and 84b have been removed by double exposure through windows 92a and 92b of pattern 90, respectively. Pattern 90 is overlaid in phantom in FIG. 4, and the removed portions of line segments 82a–82d and features 84a, 84b are also shown in phantom to enhance clarity.

Marks 101 are arranged to provide dense region 102 with approximately parallel line segments 102a, 102b, 102c, and 102d. Pattern 100 also includes reference mark 103 in the form of line segment 103a. Pattern 100 also includes assist feature region 104a with assist features 104. It should be understood that during the overlap of pattern 90 on an area previously exposed with pattern 80, that reference feature 103 is blocked from direct exposure; however, a number of reference mark portions 105a–105h can be differently impacted by various iso-dense effects. Portions 105a and 105b correspond to line segments of reference mark 103 in region 107a and dense region 102, respectively. Portions 105c and 105d of reference mark 103 are positioned between windows 92c and 92d providing the potential for some difference in iso-dense effect due to photolithographic processing in connection with these windows as compared to portions 105a and 105b. Notably, portion 105c of reference mark 103 corresponds to region 102e where features were removed by double exposure, while portion 105d of reference mark 103 is in relative isolation in isolated region 107b.

Portion 105e of reference mark 103 is located between assist features 104 in region 104a. Portion 105f and 105g of reference mark 103 are potentially subject to an iso-dense effect resulting from photolithography exposures through windows 92a and 92b. Portion 105f is in region 104b where adjacent assist features of pattern 80 were removed by exposure through windows 92a and 92b; however, portion 105g is in a relatively isolated region 107c. Portion 105h of reference mark 103 is in isolated region 107c having a lower feature density per unit area than regions 102 and 104a. It should be understood that reference mark 103 extends above and below dense feature regions 102 and 104a into different isolated regions 107a, 107b, and 107c.

While not shown to preserve clarity, it should be understood that the iso-dense effect can cause the linewidth of reference mark 103 to vary from one region to the next. In operation 126 of process 120, Scanning Electron Microscope (SEM) 75 shown in FIG. 2 is utilized to measure the linewidth of reference mark 103 at a point in region 107a (portion 105a) and at a point in region 102 (portion 105b). In operation 128, the measurement in region 102 (portion 105b) is subtracted from the measurement in region 107a (portion 105a), as determined in operation 126. This difference represents the collective iso-dense effect of both SEM 75 and the photolithographic processing to create pattern 100. In operation 130, linewidth measurements of reference mark 103 are made at a point in region 102e (portion 105c) and at a point in region 107b (portion 105d). In operation 132, the measurement for region 102e (portion 105c) is subtracted from the measurement for region 107b (portion 105d), as determined in operation 130. This difference represents the iso-dense effect of the photolithographic process alone. In operation 134, the iso-dense effect of the SEM 75 alone is determined by subtracting the difference found in operation 132 from the difference found in operation 128. Process 120 then halts.

It should be appreciated that an iso-dense effect for the assist features can be determined in a like manner. Specifically, a linewidth measurement in region 104a (portion 105e) and region 104b (portion 105f) can be determined and the difference taken to provide the photolithographic iso-dense effect peculiar to such assist features. This approach may be desirable where the assist features are of a sub-resolution type.

In one nonlimiting embodiment of the present invention, the dense line segments 102a, 102b, 102c and 102d are each about 0.2 micron in width with the spacing from the edge of one to the edge of the next being a minimum of about 0.3 micron in region 102, and are each about 0.9 microns in length. As a result, there is a center-to-center separation distance of about 0.5 micron between lines 102a and 102b, and between lines 102c and 102d. For this arrangement, assist features are of a sub-resolution type, having a length of about 0.7 micron and a width significantly less than 0.1 micron. For this embodiment, line segment 103a of reference mark 103 has a nominal length of about 6.2 microns and a width of 0.2 micron, and is approximately centered between line segments 102b and 102c with approximately a 0.5 micron center-to-center separation distance, and lengths for portions 105a–105h of about 1.0 micron, 0.9 micron, 0.8 micron, 0.7 micron, 0.7 micron, 0.7 micron, 0.8 micron, and 0.6 micron, respectively. In such an embodiment, windows 92a–92d of pattern 90 can be dimensioned and positioned to expose features defined with pattern 80 arranged in rectangles of about 0.8 micron by 1.5 microns and 0.3 micron from either side of line segment 103a to double expose the upper 0.8 micron portion of photoresist features corresponding to line segments 82a–82d and the upper 0.7 micron portion of photoresist features corresponding to assist features 84a and 84b, resulting in the removal of these upper portions.

In one form, mask 20 is prepared in this manner with chrome providing the features and areas opaque to electromagnetic radiation. In other embodiments, a photoresist film can be of a negative type as are known to those skilled in the art.

In another embodiment directed to an integrated circuit form of microdevice, a number of insulated gate field effect transistors are formed, and the iso-dense effect evaluation patterns are provided in the same layer that is used to define critical dimensions of such transistors. Additionally or alternatively, iso-dense effect evaluation patterns may be used in more than one layer, be composed of different materials, be used more or less frequently than one per field, be used in other overlapping arrangements (such as overlapping upper and lower field shot ends or field shot corners), or as would otherwise occur to those skilled in the art.

In one preferred form of the present invention, the densely spaced features in a dense feature region are separated from one another by a minimum spacing of less than about 0.5 micron. In contrast, at least a portion of one of the features in this arrangement is isolated from the features of the dense region by a distance greater than this minimum spacing. In a more preferred form, this minimum spacing is less than 0.35 micron. The principles of the present invention can be utilized to prepare any form of microdevice using techniques for which an iso-dense effect may be of concern, including but not limited to micromachines, microsensors, and/or microoptical devices, either with or without integrated circuitry.

In yet further embodiments, features of mask patterns and corresponding evaluation patterns for an iso-dense effect may not be continuous line segments. Instead, dashed line segments, or other shapes (such as circles, squares, etc.) that are continuous or discontinuous can be utilized to provide a feature. In still other embodiments, features of any given type may not follow a straight pathway, but instead may be curved or otherwise change direction, and/or the pathways of multiple features may not be approximately parallel to one another.

All publications, patents, and patent applications cited in this specification are herein incorporated by reference as if each individual publication, patent, or patent application were specifically and individually indicated to be incorporated by reference and set forth in its entirety herein. While the invention has been illustrated and described in detail in the drawings and foregoing description, the same is to be considered as illustrative and not restrictive in character, it being understood that only the preferred embodiments have been shown and described and that all changes, modifications and equivalents that come within the spirit of the inventions as defined herein or by the following claims are desired to be protected.

What is claimed is:

1. A method, comprising:
    defining a pattern on a substrate, the pattern including a plurality of features with a dense feature region comprised of a number of the features and an isolated feature region comprised of at least a portion of one of the features;
    removing a portion of one or more of the features in the dense feature region;
    making one or more measurements corresponding to at least one of the features after said removing; and
    determining an iso-dense effect from the measurements.

2. The method of claim 1, wherein the features are approximately parallel line segments and the one of the features extends from between two other of the features in the dense feature region to the isolated feature region.

3. The method of claim 1, wherein the features have a separation distance of less than about 0.35 micron from one to another in the dense feature region.

4. The method of claim 1, wherein the measurements number at least three and are each performed relative to at least three different points along a reference mark formed with the pattern.

5. The method of claim 4, wherein the measurements are made with a scanning electron microscope to determine the iso-dense effect of at least one of the scanning electron microscope and a photolithographic process.

6. The method of claim 5, wherein said defining includes performing a first exposure of a photoresist on the substrate through a first mask portion and said removing includes performing a second exposure of the portion of the one or more of the features of the dense feature region through a second mask portion.

7. The method of claim 6, which includes developing the photoresist between said removing and said making and wherein the pattern defines a layer of integrated circuitry corresponding to a critical dimension of one or more transistor gates.

8. An apparatus, comprising:
a mask to define a number of fields along a substrate, the mask including a ventral portion to define at least a portion of one or more integrated circuits, a first end portion to define a first pattern including a dense region of features each having a minimum spacing from another of less than 0.5 micron and at least one feature portion isolated from the dense region by an amount greater than the minimum spacing between members of the dense region, and a second end portion opposite the first end portion to define a second pattern including one or more windows; and wherein the mask is operable to overlap one or more of the features of the first pattern for one of the fields with the one or more windows of the second pattern for a different one of the fields to define at least one reference feature to determine an iso-dense effect.

9. The apparatus of claim 8, further comprising a wafer carrying the at least one reference feature comprised of a developed photoresist material.

10. The apparatus of claim 9, further comprising a scanning electron microscope operable to measure the at least one reference feature.

11. The apparatus of claim 8, wherein the first pattern defines the features as a group of approximately parallel line segments with the one feature portion being defined by one of the line segments extending from between two other of the line segments from the dense region of the features to an isolated region of the features.

12. The apparatus claim 8, wherein the minimum spacing is less than 0.35 micron.

* * * * *